(12) United States Patent
Lee et al.

(10) Patent No.: US 9,179,857 B2
(45) Date of Patent: Nov. 10, 2015

(54) GUIDEWIRE AND CONNECTOR THEREFOR

(75) Inventors: Chris Lee, Tewksbury, MA (US);
Christine McNamara, Chelmsford, MA (US); Ingmar Viohl, Milwaukee, WI (US)

(73) Assignee: MRI Interventions, Inc., Memphis, TN (US)

( * ) Notice: Subject to any disclaimer, the term of this patent is extended or adjusted under 35 U.S.C. 154(b) by 2253 days.

(21) Appl. No.: 10/814,972

(22) Filed: Mar. 30, 2004

(65) Prior Publication Data

US 2004/0181177 A1 Sep. 16, 2004

Related U.S. Application Data

(62) Division of application No. 09/990,878, filed on Nov. 20, 2001, now Pat. No. 6,714,809.

(60) Provisional application No. 60/252,003, filed on Nov. 20, 2000.

(51) Int. Cl.
*A61B 5/055* (2006.01)
*A61M 25/09* (2006.01)
*A61N 1/05* (2006.01)
(Continued)

(52) U.S. Cl.
CPC .............. *A61B 5/055* (2013.01); *A61M 25/09* (2013.01); *A61N 1/05* (2013.01); *G01R 33/285* (2013.01); *H01R 24/542* (2013.01); *A61B 2019/5458* (2013.01); *A61B 2562/227* (2013.01); *A61M 25/0097* (2013.01); *A61M 25/0108* (2013.01);
(Continued)

(58) Field of Classification Search
CPC ....................................................... A61B 5/055
USPC .......... 600/421–424, 410, 407, 434; 324/307, 324/309, 318, 322
See application file for complete search history.

(56) References Cited

U.S. PATENT DOCUMENTS 4,682,125 A 7/1987 Harrison et al. ................ 333/12
4,875,489 A * 10/1989 Messner et al. ............... 600/585
(Continued)

FOREIGN PATENT DOCUMENTS

EP 0 466 424 A1 1/1992
EP 0 557 127 A2 8/1993
(Continued)

OTHER PUBLICATIONS

PCT International Search Report for International Application No. PCT/US01/43295.

*Primary Examiner* — Peter Luong
(74) *Attorney, Agent, or Firm* — Lowe Graham Jones PLLC; Bruce E. Black

(57) ABSTRACT

A coaxial cable may include an inner conductor, an outer conductor coaxially disposed about the inner conductor, and a proximal end sized and shaped for insertion into a connector. The proximal end may have an outer conductor contact coupled electrically to the outer conductor, and an extended section of the inner conductor that extends axially beyond the outer conductor contact. The extended section may include an inner conductor contact having an electrically conductive material disposed at least partially around the inner conductor, and an insulated area positioned to isolate electrically the outer conductive contact from the inner conductive contact, and having an electrically insulating material disposed at least partially around the inner conductor.

35 Claims, 9 Drawing Sheets

(51) Int. Cl.
  *G01R 33/28* (2006.01)
  *H01R 24/54* (2011.01)
  *A61B 19/00* (2006.01)
  *A61M 25/00* (2006.01)
  *A61M 25/01* (2006.01)
  *H01R 9/05* (2006.01)
  *H01R 103/00* (2006.01)

(52) U.S. Cl.
  CPC ............ *H01R 9/0524* (2013.01); *H01R 2103/00* (2013.01); *H01R 2201/12* (2013.01)

(56) References Cited

U.S. PATENT DOCUMENTS

| | | | |
|---|---|---|---|
| 5,057,106 A | 10/1991 | Kasevich et al. | 606/33 |
| 5,178,159 A | 1/1993 | Christian | 600/585 |
| 5,324,311 A | 6/1994 | Acken | 607/37 |
| 5,377,682 A * | 1/1995 | Ueno et al. | 600/446 |
| 5,445,155 A | 8/1995 | Sieben | 600/443 |
| 5,601,087 A * | 2/1997 | Gunderson et al. | 600/473 |
| 5,699,801 A | 12/1997 | Atalar et al. | 128/653.2 |
| 5,738,632 A * | 4/1998 | Karasawa | 600/410 |
| 5,743,903 A * | 4/1998 | Stern et al. | 606/31 |
| 5,792,055 A | 8/1998 | McKinnon | 600/410 |
| 5,797,848 A | 8/1998 | Marian et al. | 600/459 |
| 5,868,674 A * | 2/1999 | Glowinski et al. | 600/410 |
| 5,928,145 A | 7/1999 | Ocali et al. | 600/410 |
| 6,004,269 A | 12/1999 | Crowley et al. | 600/439 |
| 6,031,375 A | 2/2000 | Atalar et al. | 324/307 |
| 6,263,229 B1 | 7/2001 | Atalar et al. | 600/423 |
| 6,284,971 B1 | 9/2001 | Atalar et al. | 174/36 |
| 6,408,202 B1 | 6/2002 | Lima et al. | 600/423 |
| 6,428,489 B1 * | 8/2002 | Jacobsen et al. | 600/585 |
| 6,549,800 B1 | 4/2003 | Atalar et al. | 600/423 |
| 6,606,513 B2 | 8/2003 | Lardo et al. | 600/411 |
| 6,628,980 B2 | 9/2003 | Atalar et al. | 600/423 |
| 6,675,033 B1 * | 1/2004 | Lardo et al. | 600/410 |
| 6,714,809 B2 | 3/2004 | Lee et al. | 600/423 |
| 6,970,742 B2 * | 11/2005 | Mann et al. | 607/23 |
| 7,689,288 B2 | 3/2010 | Stevenson et al. | |
| 7,751,903 B2 | 7/2010 | Stevenson et al. | |
| 7,822,460 B2 | 10/2010 | Halperin et al. | |
| 7,844,319 B2 | 11/2010 | Susil et al. | |
| 7,853,325 B2 | 12/2010 | Dabney et al. | |
| 2001/0056232 A1 | 12/2001 | Lardo et al. | 600/423 |
| 2002/0013540 A1 * | 1/2002 | Jacobsen et al. | 600/585 |
| 2002/0040185 A1 | 4/2002 | Atalar et al. | 600/423 |
| 2002/0045816 A1 * | 4/2002 | Atalar et al. | 600/423 |
| 2003/0028094 A1 | 2/2003 | Kumar et al. | 600/410 |
| 2003/0028095 A1 | 2/2003 | Tulley et al. | 600/422 |
| 2003/0050557 A1 | 3/2003 | Susil et al. | 600/424 |
| 2003/0199755 A1 | 10/2003 | Halperin et al. | 600/411 |
| 2004/0046557 A1 | 3/2004 | Karmarkar et al. | 324/322 |
| 2007/0288058 A1 | 12/2007 | Halperin et al. | |
| 2008/0049376 A1 | 2/2008 | Stevenson et al. | |
| 2008/0065181 A1 | 3/2008 | Stevenson | |
| 2008/0116997 A1 | 5/2008 | Dabney et al. | |
| 2008/0119919 A1 | 5/2008 | Atalar et al. | |
| 2008/0132987 A1 | 6/2008 | Westlund et al. | |
| 2008/0269591 A1 | 10/2008 | Halperin et al. | |
| 2010/0016936 A1 | 1/2010 | Stevenson et al. | |
| 2010/0023000 A1 | 1/2010 | Stevenson et al. | |
| 2010/0023095 A1 | 1/2010 | Stevenson et al. | |
| 2010/0160997 A1 | 6/2010 | Johnson et al. | |
| 2010/0168821 A1 | 7/2010 | Johnson et al. | |
| 2010/0174349 A1 | 7/2010 | Stevenson et al. | |
| 2010/0191236 A1 | 7/2010 | Johnson et al. | |
| 2010/0198312 A1 | 8/2010 | Stevenson et al. | |
| 2010/0217262 A1 | 8/2010 | Stevenson et al. | |
| 2010/0222857 A1 | 9/2010 | Halperin et al. | |
| 2010/0280584 A1 | 11/2010 | Johnson et al. | |
| 2010/0324639 A1 | 12/2010 | Stevenson et al. | |
| 2011/0022140 A1 | 1/2011 | Stevenson et al. | |
| 2011/0040343 A1 | 2/2011 | Johnson et al. | |
| 2011/0054582 A1 | 3/2011 | Dabney et al. | |

FOREIGN PATENT DOCUMENTS

| | | |
|---|---|---|
| JP | 10165404 | 6/1998 |
| WO | WO 89/11311 | 11/1989 |
| WO | WO 00/64003 | 10/2000 |

* cited by examiner

GUIDEWIRE AND CONNECTOR THEREFOR

CROSS-REFERENCE TO RELATED APPLICATION

This application is a division of U.S. patent application Ser. No. 09/990,878, filed Nov. 20, 2001, now U.S. Pat. No. 6,714,809, which claims the benefit of U.S. Provisional Patent Application No. 60/252,003, filed Nov. 20, 2000. The entire disclosure of these applications are hereby incorporated herein by reference.

BACKGROUND

The subject matter generally relates to the field of electronic connectors, more particularly to electronic connectors for use with magnetic resonance imaging guidewires.

Many percutaneous intravascular procedures use a guidewire as an initial approach of accessing a particular vessel. Once the distal guidewire tip has been placed at the area of interest, a catheter is passed over the wire from the proximal end using it as a guide to track the catheter into that vessel. In order to allow the catheter to pass, the entire length of the guidewire generally needs to fit within the lumen of the catheter.

SUMMARY

The following discloses, among other things, connectors designed to receive coaxial cables, including magnetic resonance imaging (MRI) guidewires. The following also discloses guidewires designed for insertion into connectors.

In accordance with one exemplary embodiment, a connector may include an orifice for receiving an end of a guidewire; a channel communicating with the orifice and providing an insertion path for the end of the guidewire; a first contact that is at least partly exposed to the channel, and is sized and shaped to couple with an inner conductor contact of the guidewire; a second contact that is at least partly exposed to the channel, and is sized and shaped to couple with an outer conductor contact of the guidewire; an output terminal electrically coupled to the first and second contacts; and a fastener structured and positioned to hold the end of the guidewire within the channel. The first and second contacts may be sequentially disposed along the insertion path.

The connector may include an interface circuit electrically coupled to the first and second contacts. The connector may include a connection detector exposed to the channel. The connector may include a DC blocking circuit coupled to at least one of the first and second contacts.

In accordance with another exemplary embodiment, a guidewire may include an inner conductor; an outer conductor coaxially disposed about the inner conductor; a distal end adapted for insertion into a subject to receive MRI signals; and a proximal end adapted for insertion into a connector. The proximal end may have an outer conductor contact coupled electrically to the outer conductor, and an extended section of the inner conductor that extends axially beyond the outer conductor contact. The extended section may have an inner conductor contact and an insulated area interposed between the outer conductive contact and the inner conductive contact. The inner conductor contact may have an electrically conductive material disposed at least partially around the inner conductor. The insulated area may have an electrically insulating material disposed at least partially around the inner conductor. The guidewire may include an extension attachment coupled to the proximal end of the guidewire.

In accordance with another exemplary embodiment, a medical device may include an MRI guidewire and a connector as described above.

BRIEF DESCRIPTION OF THE DRAWINGS

FIG. 9 shows the embodiment in FIG. 8 with the contacts opened to allow the guidewire to slide in.

DETAILED DESCRIPTION

Lardo et al in U.S. Pat. No. 6,675,033 (hereafter "Lardo '033"), the entire disclosure of which is herein incorporated by reference, disclose, among other things, a guidewire and associated devices for use with or as an MRI antenna. The connectors described herein may be used with any sort of guidewire or coaxial cable, not necessarily only those guidewire embodiments disclosed herein. Similarly, the guidewires disclosed herein may be used with any sort of connector, not only those embodiments disclosed herein.

Guidewires described herein may be inserted into lumens of various anatomic structures of a subject. In an embodiment, the guidewire is sized for insertion into a blood vessel. In an embodiment, the guidewire is sized for insertion into a human subject.

In MRI an external antenna (external with respect to the scanner, such as one being used as part of a guidewire) can receive electronic information from the MRI scanner. This information can be, e.g., control signals such as triggering information or transmit-receive gating signals. The antenna can provide RF signals containing, e.g., image information to be processed by the MRI scanner. The antenna can receive MRI signals generated from surrounding structures.

It would enhance the art to provide a low loss and reliable electrical connection between the antenna and the MRI scanner. It would further enhance the art to provide connectors that can be used in conjunction with guidewires, guidewire antennae, imaging needles and other antennas without diminishing the customary utility of these devices. It would also enhance the art to provide a connector that is easily removed and reattached to any contemplated guidewire, antenna, or the like.

Many MRI scanners currently known to the art are built to accommodate an external imaging antenna such as the guidewire antenna and may provide an external antenna port on the MRI scanner for that purpose. The external antenna port on an MRI scanner is often a single or multi coaxial or non-coaxial single and multi-pin connector, including BNC connectors, D-shell connectors, Lemo connectors, MMCX connectors, etc and other connectors known in the art.

Figure 1:
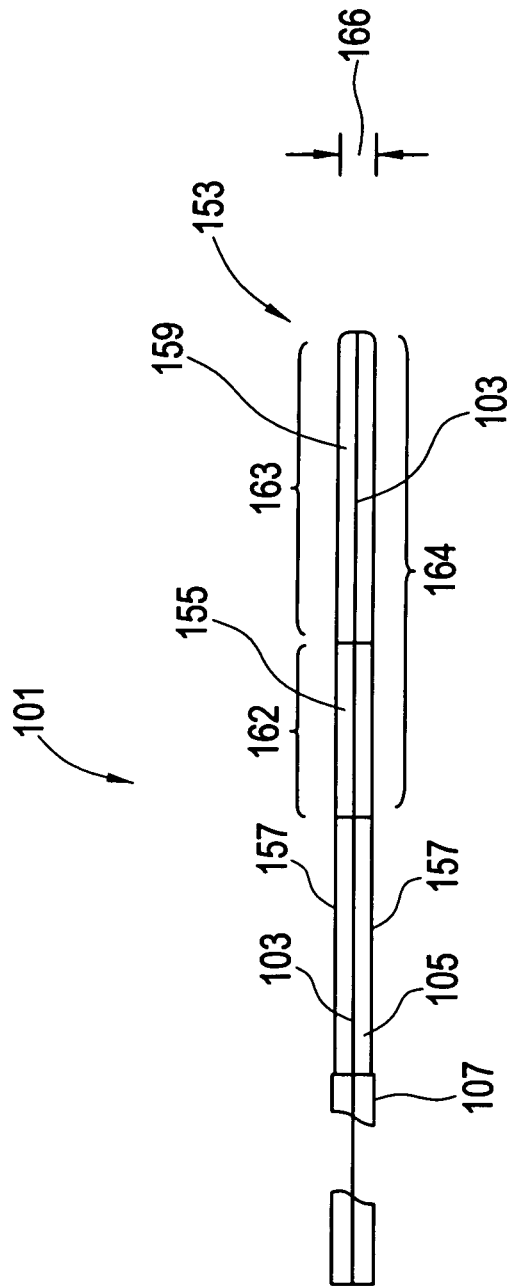
FIG. 1 shows one embodiment of the proximal end of a guidewire.

FIG. 1 shows a guidewire (101) that may be designed, in part, as a coaxial cable. Here the inner conductor (103) may be placed inside an outer conductor (157) and may be electrically separated from the outer conductor (157) by insulation (105). An additional layer of electrically insulating material (107) may be applied over the outer conductor to prevent electrical contact of the conductor to the user or patient. The outer diameter of such a guidewire may be, in one embodiment, less than about 0.040 inches, and preferably between approximately 0.012-0.038 inches. The inner conductor may have a diameter of around 0.004-0.012 inches. Materials are preferably nonferrous and nonmagnetic. This may help to prevent, e.g., image artifacts due to local magnetic field distortion, or motion of the guidewire caused by unwanted forces exerted by the magnetic field of the MRI scanner on the wire which could otherwise result in uncontrolled motion of the wire and cause harm to the patient. In an embodiment, the guidewire has a stiffness sufficient for insertion into a lumen of an anatomic structure of a subject. In an embodiment, the guidewire is sterilizable.

The distal end of the guidewire can terminate in an antenna, which could be any type of MRI antenna known to the art including looped, loopless, linear whip, or helical coil designs. An MRI antenna could be positioned anywhere along the guidewire. The guidewire may also include configurations of the distal end, such as a ribbon of a malleable substance, springs, and contoured wire shapes to improve steering of the guidewire and provide appropriate stiffness characteristics.

The guidewire can comprise a superelastic material such as the Tinol® range of materials (also known as Nitinol or NiTi). Some superelastics comprise titanium or a titanium-nickel alloy. Superelastics may be significantly deformed and still return to their original shape. These characteristics are advantageous in a guidewire due to the capacity to be severely deformed without damage and the resistance to kinking. Superelastic materials are also known for high biocompatibility and favorable mechanical characteristics within biological organisms or matter. Other biocompatible materials include, e.g., Silicone, PET, PE, Pebax, teflon, nylon, hytrel, latex, urethrane, titanium, and stainless steel.

In an embodiment, the guidewire is formed of MR-compatible materials. Examples of MR-compatible materials include but are not limited to MR-compatible stainless steel, brass, copper, bronze, Nitinol, other metallic materials that are non-magnetic, non-metallic substances such as carbon, glass fiber, or polymer, that can be plated with a layer of a good RF conductor such as copper, silver, gold, or aluminum either singly or in multiple layers, or any of the previous in any combination.

In a medical procedure, the distal end of the guidewire will be inserted into a patient, and using imaging techniques (such as MRI, X-Ray or other techniques), the guidewire will be maneuvered into a desired position, for instance near an arterial plaque. A medical device may then be threaded over the guidewire and also placed into position Often guidewires are positioned within a catheter or some other medical device, placed in a patient together, with the catheter lending support to the guidewire. This could be accomplished with a guidewire having a fixed or removable electrical connector at its proximal end by loading the guidewire into the proximal end of the catheter. A fixed connector, however, may prevent the removal or exchange of the catheter if the connector diameter is larger than the catheter's lumen diameter. In such a case, the guidewire would first be removed from the patient, the medical device exchanged, and the wire correctly placed again in the patient.

In contrast, a removable connector would permit device exchange without removing the guidewire from the patient. The connector could be removed from the guidewire, the guidewire extended with an extension wire affixed to at least a portion of the proximal end of the guidewire, the original device withdrawn, a new device inserted over the guidewire, the extension removed, and the connector reattached to the guidewire. If the medical device were a rapid exchange model, the guidewire might not need to be extended, but the connector would preferably be removed to pass the medical device over the entire length of the guidewire.

In an embodiment, the connector is formed of MR-compatible materials. Examples of MR-compatible materials include but are not limited to MR-compatible stainless steel, brass, copper, bronze, Nitinol, other metallic materials that are non-magnetic, non-metallic substances such as carbon, glass fiber, or polymer, that can be plated with a layer of a good RF conductor such as copper, silver, gold, or aluminum either singly or in multiple layers, or any of the previous in any combination.

In an embodiment, the connector may be repeatedly removed and reattached to the guidewire. This may be done, e.g., in the course of a medical procedure during which a plurality of medical devices are loaded onto and removed from the guidewire.

Such medical devices include, but are not limited to, balloon catheters for dilatation angioplasties, for stent placements, for drug infusions, and catheters for local vessel therapies such as gene therapies, radiation therapies; atherotomes and other devices for plaque resection and debulking; MRI imaging catheters; drug delivery catheters; intraluminal resecting tools; lasers and radio frequency and other ablative instruments. They could also include ultrasound imaging devices or optical coherent tomographic imaging devices. The devices would include but not be limited to those which perform a diagnostic or therapeutic role in the assessment or treatment of intravascular or intracavitary disease management.

As would be understood by one of skill in the art, in order for a guidewire to be most useful, it is preferable that a medical device be able to fit over the guidewire and for the device to be capable of placement over the guidewire after the guidewire is in position.

In order to connect the guidewire to the MRI machine's electrical signals so as to make it useful as an antenna, however, it is preferable to enable the very small guidewire to connect to the external antenna port on the MRI scanner, typically through a BNC connector, a multi-pin connector, or other connector. In one embodiment, the connector could be permanently attached to the proximal end of the guidewire. In another embodiment, the connector may be removably attached to the proximal end of the guidewire. In another embodiment, the connector may be dimensionally adapted to allow the catheter or other medical device to be placed over both the connector and the guidewire. In another embodiment, the proximal end of the guidewire may be dimensionally adapted to have relatively the same diameter as the rest of the guidewire.

The proximal end of the guidewire can be specially designed to provide surfaces for connecting to both inner and outer coaxial conductors while maintaining mechanical strength and not risking breakage or bad connection from having to thread the narrow inner conductor directly into some type of fitting capable of making an electrical connection.

Similarly, the proximal end can be adapted to fit an extension wire to permit device exchange capability as well as the electrical connection.

FIG. 1 shows the proximal end of a guidewire utilizing one embodiment to make connection to the inner conductor in some embodiments simpler and more reliable. In FIG. 1, the inner conductor (103) and the outer conductor (157) extend beyond the end of the outer insulation (107) to expose conductive areas for electrical contact. The inner conductor (103) extends further, beyond the proximal end of the outer conductor (157), thereby exposing an extended section (164) on which to make contact to the inner conductor (103). The extended section has an insulated area (162) and an inner conductor contact (163). The inner conductor contact (163) includes an electrically conductive material (159) that may be built up around the inner conductor (103). This facilitates the easy insertion of the proximal end (153) of the guidewire (101) into the connector, and helps to maintain maximum strength in the extended section (164). In an embodiment, the inner conductor (103) may be built up with electrically conductive material, preferably nonmagnetic (such as brass tubing) to approximately the same diameter (166) as the outer conductor (157). The inner conductor contact (163) may be radially disposed about a portion of the extended section (164). In an embodiment, the inner conductor contact (163) is built up to a smaller diameter than that of the outer conductor (157). In an embodiment, the inner conductor contact (163) is built up to a larger diameter than that of the outer conductor (157).

Figure 6:
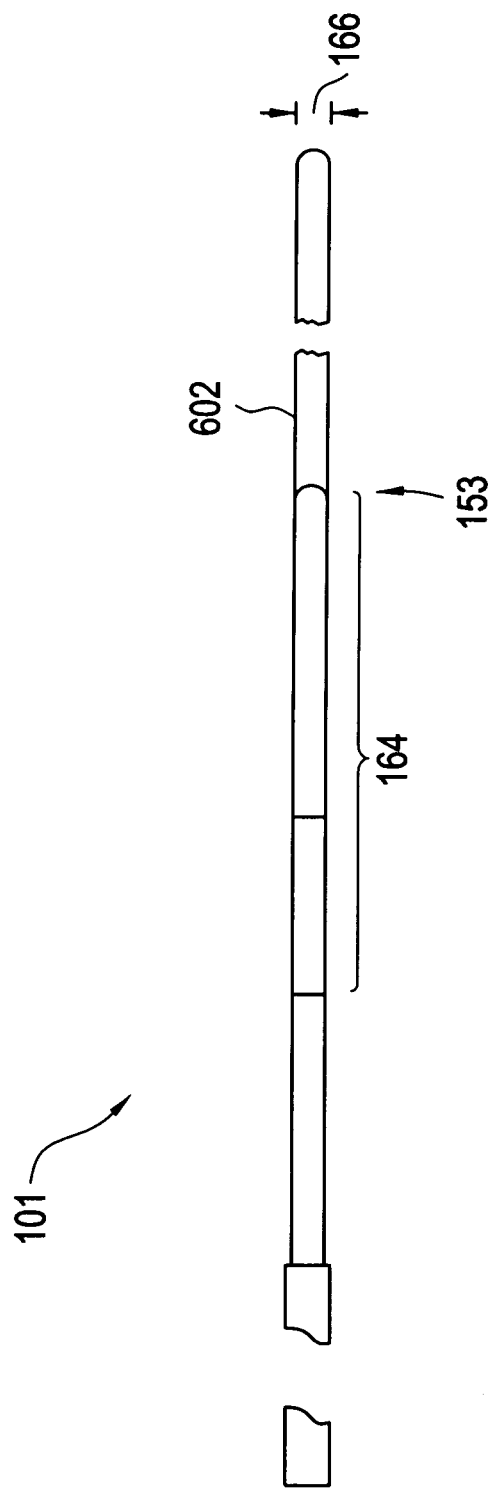
FIG. 6 shows an embodiment of a guidewire with an extension attachment.

As shown in FIG. 6, at least a portion of the extended section (164) may be configured to accept an extension attachment (602). In an embodiment, the attachment (602) has a diameter substantially equal to diameter (166) as the guidewire (101). The extension attachment can add a length to the proximal end (153) of the guidewire (101) that may be long enough to permit medical device exchanges without displacing the guidewire (101) from its position in-situ. The attachment mechanism may include, but is not limited to: matching threads on the attachment and extended section (164) for screwable attachment; a tube to tube slip fit or snap fit; or a coiled spring fitting into a appropriately sized tube. Any of these configurations could be interchangeably incorporated on any portion of extended section (164) area of the guidewire (101), or the extension attachment. Other attachment mechanisms known in the art may also be employed. In an embodiment, the extension attachment is attached to the inner conductor.

Referring again to FIG. 1, the insulated area (162) can be built up with an electrically insulating material (155) to prevent potential short circuiting between the outer conductor (157) and the inner conductor (103) or inner conductor contact (163). The built-up insulating material (155) can also provide rigidity for the proximal end (153).

This configuration converts the two concentric coaxially oriented conductors to a pair of contacts that are exposed to the connector in a sequential axial configuration, both of which are relatively the same diameter as the outer conductor. In one embodiment, the coaxial relationship can then be maintained by the design of the connector from that point to an interface circuit, or the MRI scanner, while still allowing for easier connection to the connector.

The interface circuit may include capacitors, inductors, resistors, diodes, and other electrical and electronic elements to couple the signals from the guidewire (101) ultimately to an MRI scanner. The interface circuit may be coupled to each of the contacts in the connector. The interface circuit may include a tuning/matching circuit. The interface circuit may include a decoupling circuit. The interface circuit may include a balun trap. The interface circuit may also provide high voltage protection for the guidewire and any subject into which the guidewire may be inserted during use. DC in excess of a predetermined threshold may be isolated from the electrical signal applied to the guidewire via DC blocking/RF bypass capacitors. The interface circuit may also include a connection detector to signal the user or scanner in the event of disconnection between the guidewire and connector. The interface circuit may also include an identification system to identify the coil to the connector or to the scanner with a coding scheme.

The connector adapted for coupling to the inner conductor contact (163) can be of many types; exemplary embodiments are provided below. One of skill in the art would recognize additional connector types and those types are also included in this disclosure.

Figure 2:
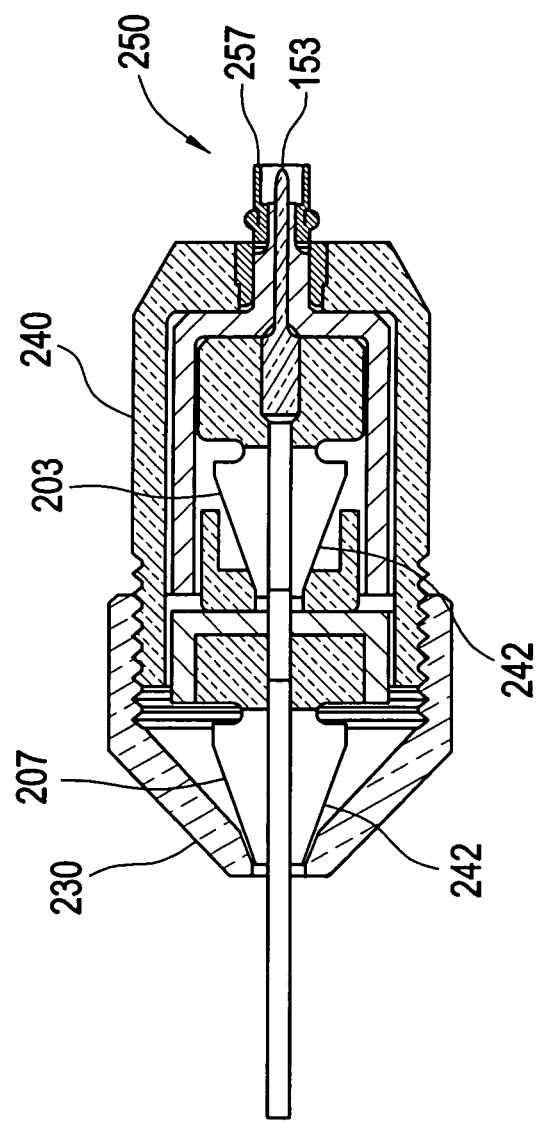
FIG. 2 shows one embodiment of a collet style clamping connector.
Figure 3:
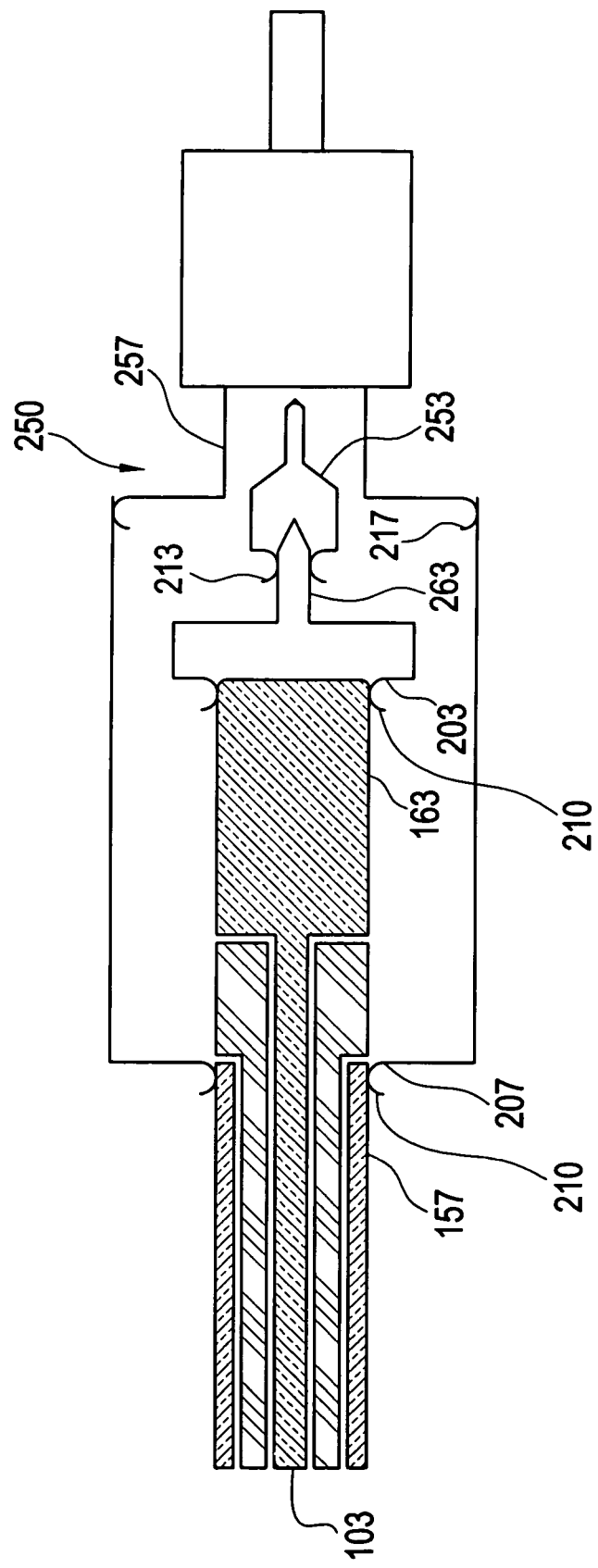
FIG. 3 shows one embodiment of the internal connection detail of a collet style connector such as that shown in FIG. 2.

In an embodiment, two conductive collets are positioned in line coaxially with the guidewire, as shown in FIG. 3. A first collet (203) makes contact with the inner conductor contact (163) of the inner conductor (103). A second collet (207) makes contact with the outer conductor (157). These two collets remain electrically isolated from each other. Isolation may be maintained by, e.g., physical separation or by imposition of an insulating material between them. The collets may come into contact with the appropriate conductors through any method or system known to the art. One method is to compress the collets axially to provide a clamping force on the guidewire contact surfaces via the angled outer surface (210) of the collets. This can be achieved using a cap with threads or with cams to produce axial motion when rotated relative to the body of the connector. One embodiment of such a cap (230) and tapered collets (203, 207) is shown in FIG. 2. In an embodiment, the collets are flexible and resilient.

When connecting the guidewire to the connector, the connection between the outer conductor contact (157) and the distal collet (207) contact can be easily confirmed manually by lightly tugging or twisting the guidewire relative to the connector. Mechanical clamping may be desirable in one embodiment because it can, e.g., facilitate steering the guidewire. A physician or other operator of the guidewire can use the connector as a handle. Mechanical clamping can also prevent inadvertent removal of the guidewire from the connector. The increased diameter (and potential gripability through texturing of the body (240)) of the connector can enable the operator to achieve greater torque control on the guidewire as a whole and at the distal tip where steering is performed. The increased torque control can improve the ability of the operator to steer the guidewire through twisting pathways.

In an embodiment, the inner and outer conductor contacts can form annular shapes. In an embodiment, the insulated area may form an annular shape. In an embodiment, any of the inner conductor contact, the outer conductor contact, and the insulated area may form a "C" shape. In an embodiment, any of the inner conductor contact, the outer conductor contact, and the insulated area may form a series of interrupted patches around the circumference of the guidewire.

In an embodiment, the proximal contact may couple to the outer conductor contact, and the distal contact may couple to the inner conductor contact.

To ensure a good mechanical and electrical contact is made on the enclosed inner conductor, the clamping angle of the proximal collet (203) can be reduced so that it will clamp the inner conductor contact before the distal collet (203) will clamp the outer conductor under axial movement. Therefore when the outer conductor contact is confirmed manually, the inner contact is also ensured.

In operation, the cap of FIG. 2 would slowly compress the collets (203) and (207) as the cap (230) may be screwably displaced along the connector body (240) by pushing relatively solid components of the cap or body into the angled sides (242) of the collets. One of skill in the art would recognize that many other attachment methods other than screwably connecting could be used and all such other methods are included within the scope of this disclosure. Some alternatives to the threads or cams for axial locking motion include, but are not limited to, a lever that may be integrated into the connector body to produce this action or an axially sliding sleeve with a return spring and/or detents.

In order to maintain the coaxial nature of the conductors, such as for providing shielding, the signal path for the outer conductor (157) may be from the distal collet (207) to the cap (230) and body (240) of the connector, and to the outer sleeve (257) of the rotating contact (250). This rotating contact can be any type of coaxial (or other if the coaxial nature is not desired to be maintained) connector such as a standard BNC connector, or a standard MMCX connector, or any other standard or nonstandard connectors known in the art now or in the future. In one embodiment, this contact (250) can then be connected by any method known in the art, to the antenna output of the MRI scanner including, but not limited to, the use of a cable, or by methods of wireless transmission.

The signal path for the inner conductor (103) may be from the proximal collet (203) to a center pin (263) which can be connected directly to, or be made from the same contiguous part as, the inner pin (253) of the contact (250). In an embodiment, the proximal collet (203) and center pin (263) are disposed inside the outer signal path to maintain coaxiality throughout the connector. In an embodiment, one or both of the proximal collet (203) and center pin (263) are not disposed inside the outer signal path. In an embodiment, the contacting components may be plated with an oxidation resistant material such as gold to enhance connection quality. Further, in one embodiment, additional rotating contacts (213) and (217) as shown, e.g., in FIG. 3, may be provided to enable rotation of the connector relative to any cables or devices connected to the output terminal. This rotational capability of the connector can also be accomplished through coaxial contacts with a smooth sliding fit to the stationary socket.

Figure 5:
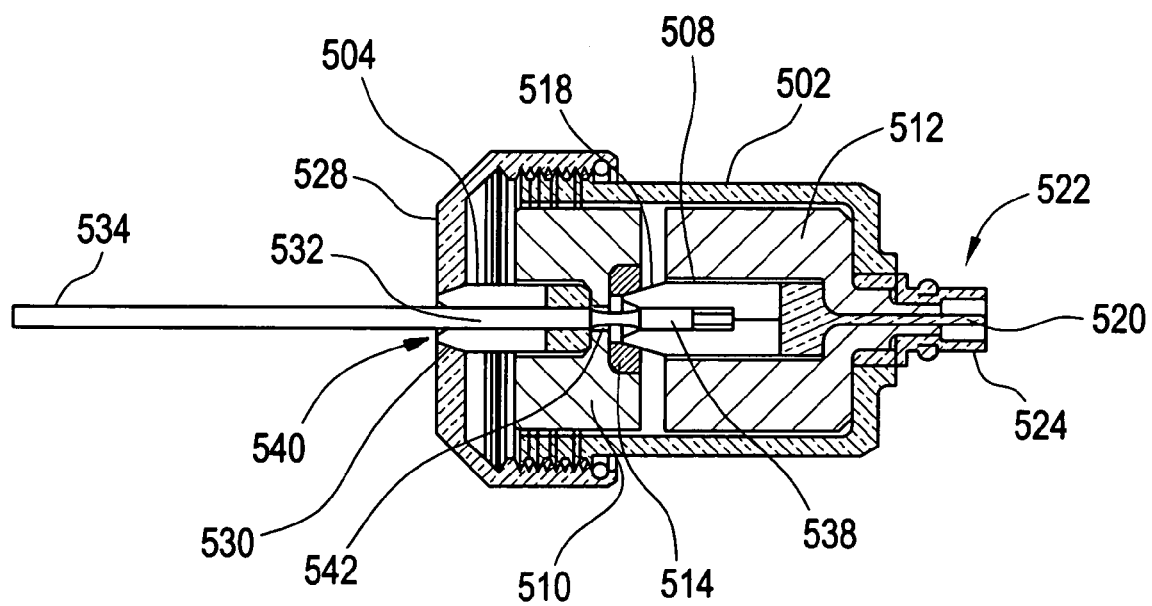
FIG. 5 shows another embodiment of a collet style clamping connector.

FIG. 5 shows another embodiment of a collet style clamping connector. The body (502) may contain a distal collet clamp (504) and a proximal collet clamp (508) arranged longitudinally. A distal insulator (510) may surround the distal collet clamp (504) and insulate it from the body (502) and/or from the proximal collet clamp (508). The distal insulator (510) may also center the distal collet clamp (504) in the body (502). The distal insulator (510) may include a material having a dielectric constant. A proximal insulator (512) can similarly surround the proximal collet clamp (508) and may include a material having a dielectric constant. The proximal insulator (512) may insulate the proximal collet clamp (508) from the body (502) and/or from the distal collet clamp (504). A proximal clamp ring (514) may be positioned between the distal collet clamp (504) and the proximal collet clamp (508), contacting the distal insulator (510) and engaging the angled surface (518) of the proximal collet clamp (508). The distal insulator (510) may insulate the distal collet clamp (504) from the proximal clamp ring (514). The distal and proximal clamps (504, 508) may also be insulated from each other by physical isolation from one another. On the end opposite the angled surface (518), the proximal collet clamp (508) can terminate in a center pin (520) of a plug (522).

The plug (522) may be an output terminal including a single or multi coaxial pin or non-coaxial single and multi-pin connector, including BNC connectors, D-shell connectors, Lemo connectors, MMCX connectors, etc and other connectors known in the art. In an embodiment, the proximal contact (508) may extend axially to the plug (522) to form the center pin (520). The center pin (520) may be surrounded by an outer adapter (524). The plug (522) can have a mechanism for secure but rotatable and removable attachment to a mated connector (not shown). The mechanism may include, e.g., a spring-loaded cuff (528) that fits into a corresponding retaining ring or groove of the mated connector. A cap (528) may screwably attach to the body (502).

A guidewire (534) may be inserted into the connector through an orifice (540) and into a channel (542). The channel (542) may define an insertion path for an end of the guidewire (534) in to the connector. The cap (528) may then be screwed onto the body (502), to secure the guidewire (534) in the connector and to form electrical contacts. The cap (528) can engage an angled surface (530) of the distal collet clamp (504). This may cause the distal collet clamp (504) to touch an outer conductor contact (532) of the guidewire (534). Compression of the cap (528) against the distal collet clamp (504) may also cause the distal collet clamp (504) to push against the proximal clamp ring (514), which in turn can engage the angled surface (518) of the proximal collet clamp (508), causing it to touch a inner conductor contact (538) of the guidewire (534).

An electrical signal from the inner conductor contact (538) of the guidewire (534) can follow an inner conductor path that may include the proximal collet clamp (508) and the center pin (520) of the plug (522). In an embodiment, the inner conductor contact (not shown) of the guidewire (534) extends axially to the plug (522) to form the center pin (520). An electrical signal from the outer conductor contact (532) of the guidewire (534) can follow an outer conductor path that may include the cap (528), the body (502), and the outer adapter (524) of the plug (522).

Any of the contacts described herein may have an annular shape; may extend around the full circumference of the channel; may extend around a portion of the circumference of the channel; may extend around multiple portions of the circumference of the channel; or may extend around the full circumference of the channel with interruptions.

The impedance of the connector can be matched to that of any MRI scanner by adjusting the relative dimensions of the inner and outer conductor paths and the dielectric constants of the insulators (510, 512). The materials of the insulators (510, 512) may be any electrically insulating substance or air. In an embodiment, the insulators (510, 512) include a fluoropolymer. The insulators (510, 512) may include polyethylene, a foamed material incorporating air in the structure, ceramic, or other materials with appropriate dielectric and mechanical properties.

The guidewire (534) may be secured in the connector by other securing mechanisms. In an embodiment, the connector includes a gripper that contacts the guidewire (534) and holds in relative longitudinal position with respect to the guidewire.

The gripper may be actuated by, e.g., a lever, collet, snap, button, dial, cam, or other device known to one of skill in the art.

In an embodiment, the connector may be provided with a sliding contact. This may take the form of, e.g., a spring piston on the inside of the channel (542) through which the guidewire (534) inserts. The piston can push against the guidewire (534), releasably making electrical contact.

In an embodiment, the connector may be provided with a coil wound against the inner wall of the channel (542). The coil may be dimensionally adapted to releasably grip the guidewire (534) as it is inserted into the channel (542). The coil can be deformed, e.g., by bending, tilting, or pressing out of round, to allow enough radial deflection to prevent binding of the guidewire (534) during, e.g., insertion or removal.

In an embodiment, the channel (542) may be provided with slots, dimples, or dents. These permit the channel (542) to expand slightly during insertion of the guidewire (534) and to grip the guidewire (534).

In an embodiment, a tubular mesh of wire may be deployed within the channel (542). As the guidewire (534) is inserted, axial compressive force may be exerted on the mesh by the guidewire, causing its diameter to increase slightly and permit further insertion of the guidewire (534). Once the guidewire (534) is inserted, the mesh can remain in contact with it.

In an embodiment, the guidewire (534) may be rotationally fixed with respect to the connector. This facilitates rotation of the guidewire by gripping and rotating the connector. Such a manipulation may be desirable, e.g., to rotate a portion of the guidewire (534) that is inside a subject. The connector may be rotationally free with respect to the mated connector. This prevents the creation of torsion in the guidewire (534) or at the point of connection of the plug (522) to the mated connector.

In an embodiment, the guidewire could be secured and rotationally fixed with respect to the connector by screwably attaching the guidewire to the connector. Threads could be provided on, e.g., the outer contact and/or inner contact of the guidewire, with corresponding threads on the distal and/or proximal contact of the connector.

Figure 8:
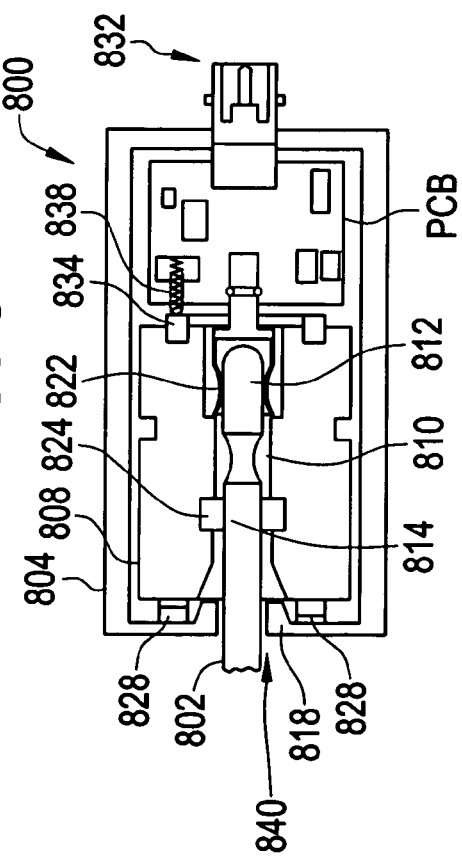
FIG. 8 shows an embodiment of a clamping connector that permits rotation of a guidewire relative to the connector.

FIG. 8 shows an embodiment in which the guidewire (802) may be rotationally free with respect to the connector (800). In another embodiment the connector body (804) provides RF shielding by using an electrically conductive material or by applying a conductive layer to a non-conductive body material.

The connector (800) may include a contact carrier (808). The contact carrier (808) may be made of a non-conducting material. It can hold one or more contacts (822, 824) exposed to a channel (810) to connect to the guidewire contacts (812, 814) electrically, and mechanically connect to at least one surface of the guidewire (802) with sufficient force to retain the guidewire (802) while being pulled axially. The contact carrier (808) may surround the channel (810). When the carrier (808) is in its closed (free) state, the contacts (822, 824) exposed to the channel (810) are in contact with the guidewire contacts (812, 814).

Figure 9:
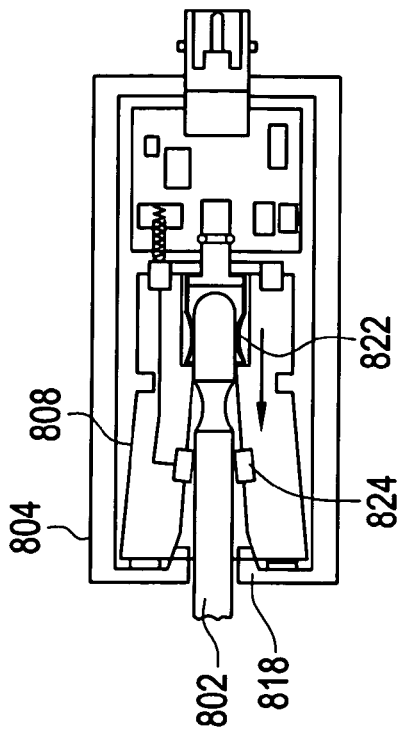

The carrier (808) can be spring loaded (as by, e.g., springs 828) or include an elastically bendable material allowing it to be deformed by pushing it against a conical wedge (818) at the front of the body (804) and disposed between the carrier (808) and an orifice (840). The springs (828) may be disposed between the wedge (818) and the carrier (808). The carrier (808) may optionally be made pliable by providing, e.g., slots (1002 in FIG. 10) or other interruptions in the carrier (808). This deformation can open the carrier (808) radially, moving at least one of the contacts (822, 824) outward, as shown in FIG. 9. This opening provides clearance for the guidewire (802) to be inserted with less interference than for the carrier (808) in the closed (free) position. When released, the carrier (808) will return to its free position by sliding proximally and off of the wedge (818), allowing the contacts (822, 824) to clamp the guidewire (802) and allowing the carrier (808) to rotate relative to the body (804). In an embodiment, the contacts (822, 824) present no obstructions to the free rotation of the guidewire (802) within the channel (810).

Figure 10:
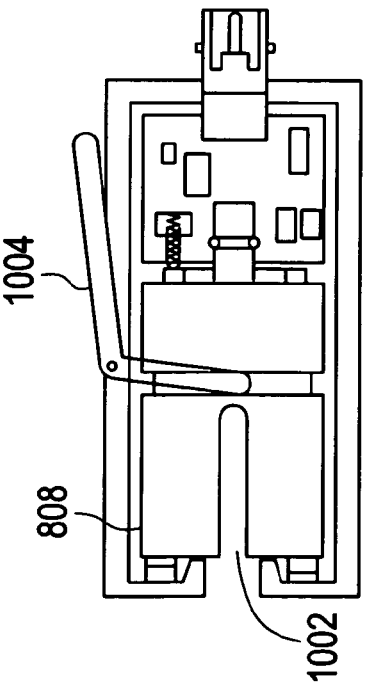
FIG. 10 shows a cutaway view of an embodiment of a clamping connector with a securing mechanism having a lever.

The carrier can be actuated (i.e., moved from the closed or free position to an open position) by a number of mechanisms, such as by a lever (1004) as shown in the cutaway view of FIG. 10. In an embodiment, the lever (1004) may be depressed, thereby moving the carrier (808) distally and causing it to open. A lever facing in the opposite direction and lifted to actuate the carrier (808) can also be used. Alternatively, the connector can be configured such that axial movement can be produced when one component can be rotated relative to another, as with a cam or threads. A slide or button could also be used.

In an embodiment, e.g., as shown in FIG. 8, the outer contact (824) can be provided as an active clamping contact that may be applied to and released from the guidewire (802) via actuation of the carrier (808). This provides electrical contact and good mechanical clamping on the outer contact (814) of the guidewire (802), which may be stronger than that of the inner conductor (812). This may make the outer contact (814) a preferred portion of the guidewire (802) for mechanically fixing the guidewire (802) to the carrier (808). The outer connecter contact (824) can have one or more conductive parts mounted in the carrier (808) and connected to a rotatable contact behind or outside the carrier. This can be done using a conductive ring (834) in slidable contact with a spring-loaded plunger (838) or with a stamped flat contact. These may be mounted on a printed circuit board (PCB) or directly to the outer adapter of, e.g., a BNC (832) or to the body (804). In another embodiment, the distal contact may be a passive slip type contact and the guidewire is mechanically fixed to the carrier in a location other than the distal contact.

The inner contact (822) can be, e.g., an active clamping, or a passive slip fit type of contact. As a passive contact, it could contact the proximal guidewire contact (812) using, e.g.: a wire oriented perpendicular to the channel and having a surface tangent to the channel; a patch, strip, or ring of formed or stamped metal placed adjacent to the channel; a coiled or deformed coil spring, providing a contact and gripping surface; a tube modified with slits or dimples to permit expansion and clamping; or with a tubular mesh that can expand or clamp with axial movement of the guidewire. A portion of a formed contact, e.g., the end exposed to the channel, may be oriented tangentially with respect to the channel. The inner contact (822) may include a spring-loaded piston which allows the wire to pass but maintains contact while in place.

An electrical signal received by any of these types of contacts may be coupled to, e.g., a ring (834), an outer adapter of a connector, or the connector body. In addition to the rotational movement this can allow axial movement via sliding or flexible contact to allow the carrier to be actuated. A coil spring may be deformed on it perimeter, i.e., by bending the turns of the coil out of round to conform to, e.g., a triangular or rectangular shape. Such perimeter deformation can provide an electrical contact and can provide gripping and removal resistance. A spring may also be longitudinally deformed, in which the spring is bent away from its straight-line shape, so that it can provide an electrical contact and can provide gripping and removal resistance.

The outer contact (824) may also have a wire, a patch or ring of formed or stamped metal, a spring, tube, or mesh, as described above.

Figure 11:
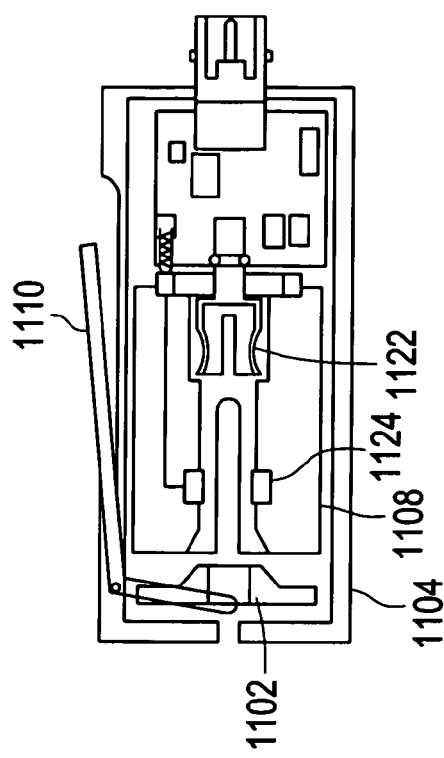
FIG. 11 shows another embodiment of a clamping connector with a securing mechanism having a lever.

FIG. 11 shows an embodiment wherein the wedge (1102) can be separate from the connector body (1104). This facilitates the actuation of the carrier (1108) to open the at least one of the proximal and distal contacts (1122, 1124) without the need for axial movement of the carrier (1108), thereby simplifying the electrical connections from the carrier (1108) to the body (1104) of the connector. Actuation can be accomplished, e.g., by lifting a lever (1110) away from the body (1104), causing the wedge (1102) to move into the carrier (1108). Other securing mechanisms described herein and known to the art may also be employed.

In an embodiment, additional contacts can be incorporated into the guidewire channel to provide any contacts needed for detecting the presence or absence of the guidewire contact.

Figure 4:
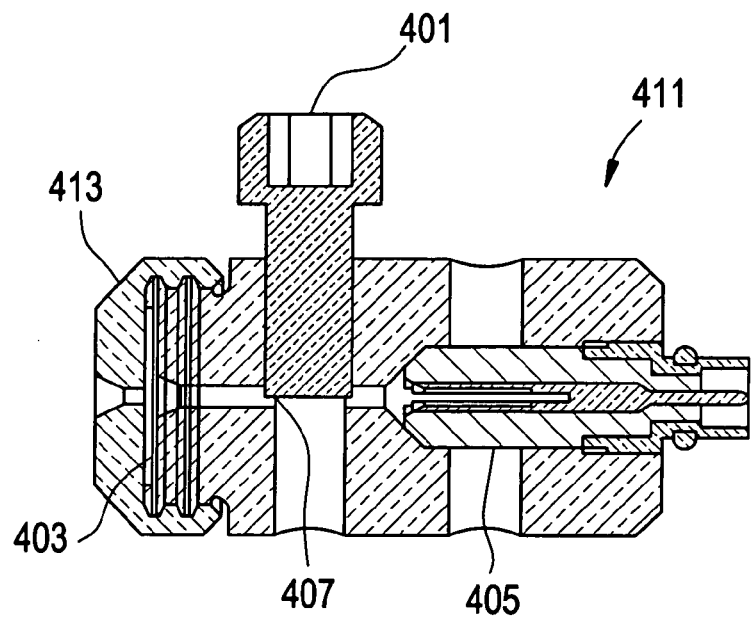
FIG. 4 shows one embodiment of a Radial/Tubular clamping connector.

In another embodiment depicted in FIG. 4, the connector (411) may include a pair of coaxial tubular contacts. The proximal contact section of the guidewire may be inserted into the connector to couple with the contacts. These contacts could include, e.g., a slip fit on the guidewire contacts, or an active radial clamping action that can be applied to positively hold the tubular contacts on the guidewire contacts. These could also be combined, such as a sliding contact (405) for the inner conductor/proximal connection and a radially clamping contact (407) for the outer conductor/distal connection.

An active clamping configuration has the advantage of a secure mechanical connection when electrically connected, allowing the connection to withstand some tensile and torsional loading while the guidewire is manipulated. Radial clamping action can be applied by, e.g., a screw, spring, plunger or lever (401), which can be levered to compress, bend, or apply friction to the guidewire when it is within the connector tubes. The tubes could be made from a conductive material with slots to allow flex for clamping, or alternatively from a metal spring or a flexible conductive material, such as a plastic with an electrically conductive coating or filler.

Because intravascular procedures commonly result in some blood or other bodily fluids on the operators' gloved hands, it may be desirable to position a wiper or seal at the entry of the connector, and such a wiper can be included in any type of connector in an embodiment. Saline solution and other fluids are also commonly present during these procedures. This wiper would minimize the introduction of fluids and other contamination into the connector by wiping the surface of the guidewire tip as it is inserted into the connector and block spilled fluids from entering the connector. The entry of such fluids into the connector could increase signal noise from degradation of the connection, or could cause a failure in the operation of the guidewire as an antenna. This wiper can be made from a soft flexible material such as silicone. It could have slits and/or a hole to allow passage of the guidewire into the connector or the guidewire could be contoured so as to punch a hole through the wiper upon insertion. One embodiment of a wiper (403) is depicted in FIG. 4. In an embodiment, the wiper (403) can be disposed within a wiper cap (413). In an embodiment, the wiper cap (413) screwably attaches to the remainder of the connector (411).

Connectors may be removable from the guidewire when desired by the operator. Further, a medical device can be threaded over a guidewire without having to overcome significant variations in diameter. Therefore the guidewire can be placed in position, the connector can be removed allowing a catheter to be threaded over the guidewire, and the connector can be reattached to enable additional imaging with the catheter in place.

In an embodiment, the housing for the connector also contains an interface circuit, such as one described in Lardo '033, for the MRI scanner. This would provide the benefit of a single component for the user to connect and coordinate during the procedure.

Figure 7:
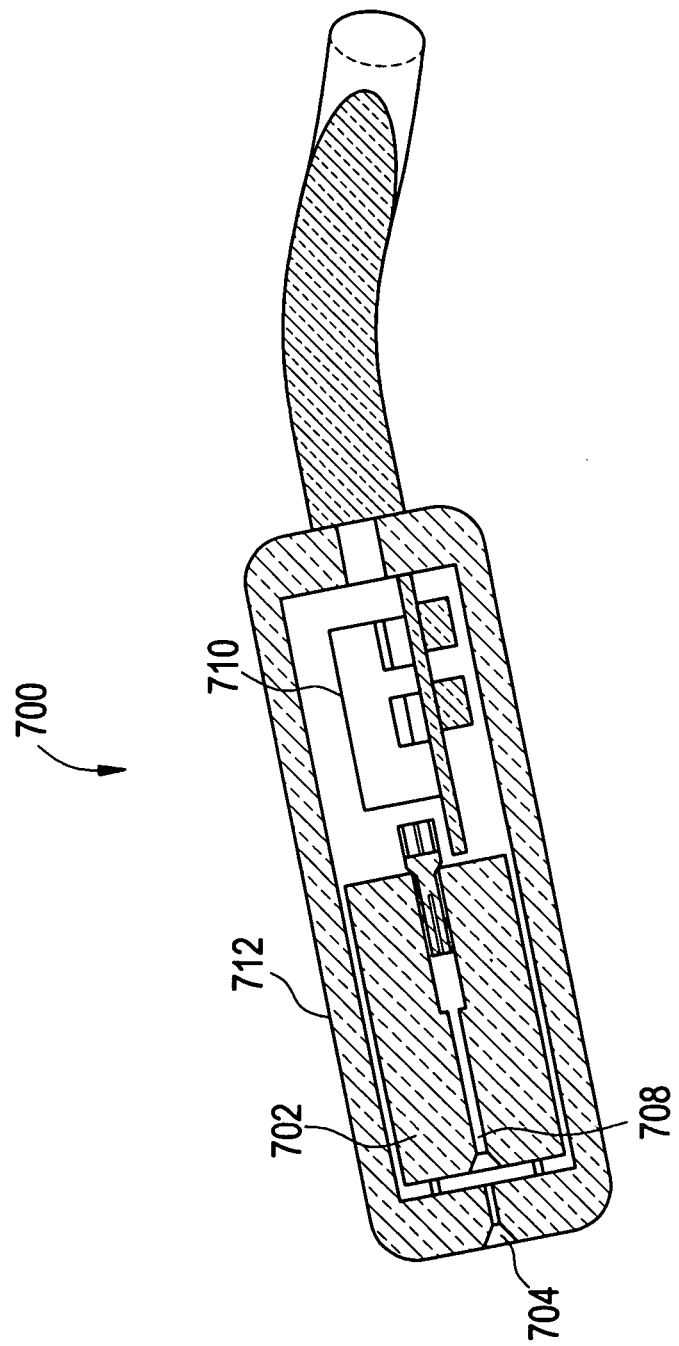
FIG. 7 shows one embodiment of a connector integrated with an interface circuit.

As depicted in FIG. 7, the interface circuit and the connector may be combined in a single housing as a combined connector (700). Such an arrangement eliminates one connection that links the guidewire to the MRI scanner. This can make the system more reliable, can lessen the risk of disconnection during operation, can reduce cost of the system, and can reduce the number of discrete parts that must be handled by operators of the MRI imaging apparatus.

A guidewire may be inserted through an orifice (704) into a channel (708) within the contact carrier (702). The guidewire may be secured in the contact carrier (702) by any of the securing mechanisms described herein or known to one of skill in the art.

In any of the embodiments described herein, the body of the connector can provide shielding to prevent RF interference by use of a conductive material for the body, or a conductive layer on a nonconductive material. All materials are preferably nonmagnetic to prevent interaction with the magnetic field of the MR scanner.

Any arrangement of guidewire contacts described herein or known to one of skill in the art may be deployed within a contact carrier (702) of the combined connector (700). An interface circuit (710) may be arranged adjacent to the contact carrier (702) and within a common housing (712). The guidewire contacts are electrically coupled to the interface circuit using any type of electrical contact configuration, such as a coaxial connector, individual sliding or rotating contacts or hardwire connection.

Use of the combined connector may substantially diminish the risk of guidewire disconnection from the interface circuit during operation. This risk can be troublesome because the guidewire antenna can cause RF heating of the tissue surrounding it if not appropriately connected to the interface circuit during use, e.g., the transmit cycle of the MR imaging sequence.

To guard further against unintentional disconnection of the guidewire from the interface circuit, the connector may further include a connection detector. The connection detector may be exposed to the channel. The detector circuit may couple with at least one of the contacts in the connector. The detector circuit can couple with a standalone detector. The detector circuit may cause an alarm to be tripped in order to notify an operator or technician that a disconnection has occurred. The detector circuit may also couple with the MRI systems control signals to, e.g., notify the user and/or terminate the scan in case of a disconnect from the system.

An example of a connection detector can be a pair of contacts that form a closed circuit when they touch one or more of the guidewire contacts. The closed circuit could power an LED display, alarm, or indicator. Such a display, alarm, or indicator can provide constant reassurance to the operator or control room technician that the guidewire is connected, or could notify the operator or technician that disconnection has occurred. The closed circuit could also function as an interlock with the MRI system supplied control signals.

Figure 12:
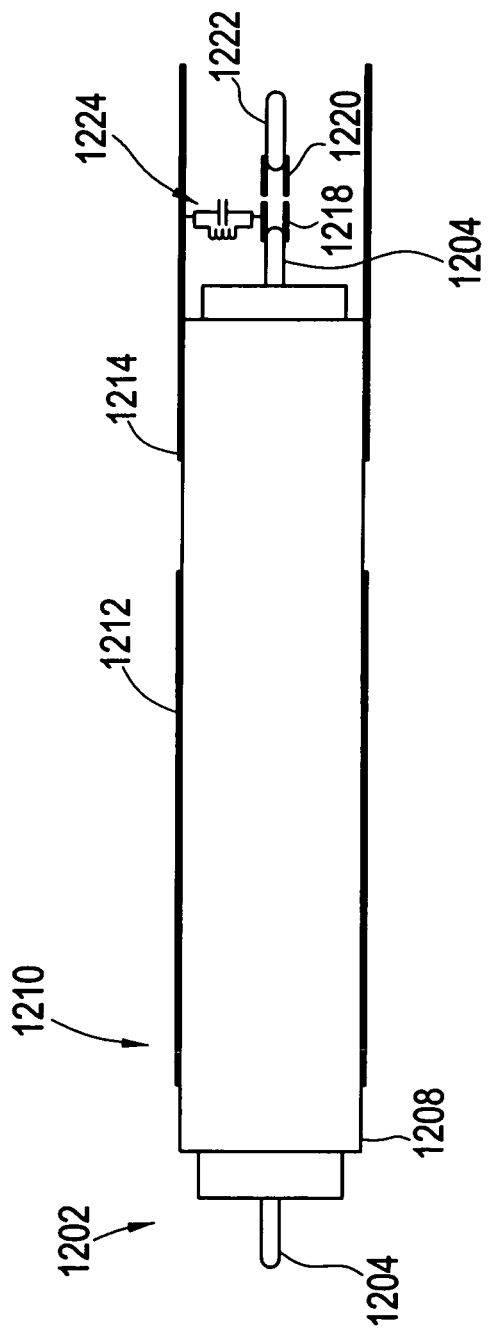
FIG. 12 shows an embodiment of a connector having a connection detector.

In an embodiment shown in FIG. 12, the proximal end of the guidewire (1202) having an inner conductor (1204) and outer conductor (1208) can be inserted into the distal end of the connector (1210). As the guidewire (1202) can be advanced through the connector, the outer conductor (1208) can bridge the gap between distal and proximal connector contacts (1212, 1214). The inner conductor (1204) can bridge the gap between distal and proximal inner contacts (1218, 1220). A control signal supplied from the system side on a center pin (1222) can thus be routed through a detector circuit, such as the capacitor/inductor combination (1224), onto the outer conductor (1208), and thence to the system.

Another example of a connection detector may be a mechanical switch deployed within the channel of the connector, into which the guidewire can be inserted. When fully inserted, the guidewire actuates this switch, closing a circuit or otherwise permitting transmission of a connection signal.

Another example of a connection detector contemplates the closure and/or securing of the guidewire within the connector to be contingent upon full insertion of the guidewire. A lever, cam, button, or other such device used to secure the guidewire in the connector may be arranged so that it can be actuated by a fully inserted guidewire, or that it can not be actuated unless the guidewire is fully inserted.

In another example, a light source can be positioned to emit light into the channel. A detector monitors the emitted light. In an embodiment, insertion of the guidewire obscures the light. The detector senses that the received light is diminished and thereby fails to send a disconnect signal. In another embodiment, the detector may send a connect signal as long as the guidewire is obscuring the emitted light.

In another example, a light source can be positioned to emit light into the channel. A detector monitors the emitted light. The emitted light is directed such that it is not received by the detector in the absence of a fully inserted guidewire. In an embodiment, insertion of the guidewire alters the emitted light path. In an embodiment, insertion of the guidewire causes the emitted light to be reflected or refracted so that it is received by the detector. The detector may send a connect signal when the guidewire is sufficiently inserted. The detector may send a disconnect signal when the guidewire is insufficiently inserted.

In another example, an activated LED may be positioned on one side of the channel, and a detector monitors the light emitted therefrom. Full insertion of a guidewire could obstruct the emitted light path or change the pattern of reflection and thereby permit detection of the insertion. In another example, the connector may be provided with source and detector optical fibers. Full insertion of the guidewire could create an imposition between the two fibers, disrupting reflection and facilitating detection of full guidewire insertion. In another example, the source fiber may conduct light from a light source external to the conductor.

In another example, an inductive or capacitive sensor may be integrated into the connector so that the presence of the guidewire can be detected.

Figure 13:
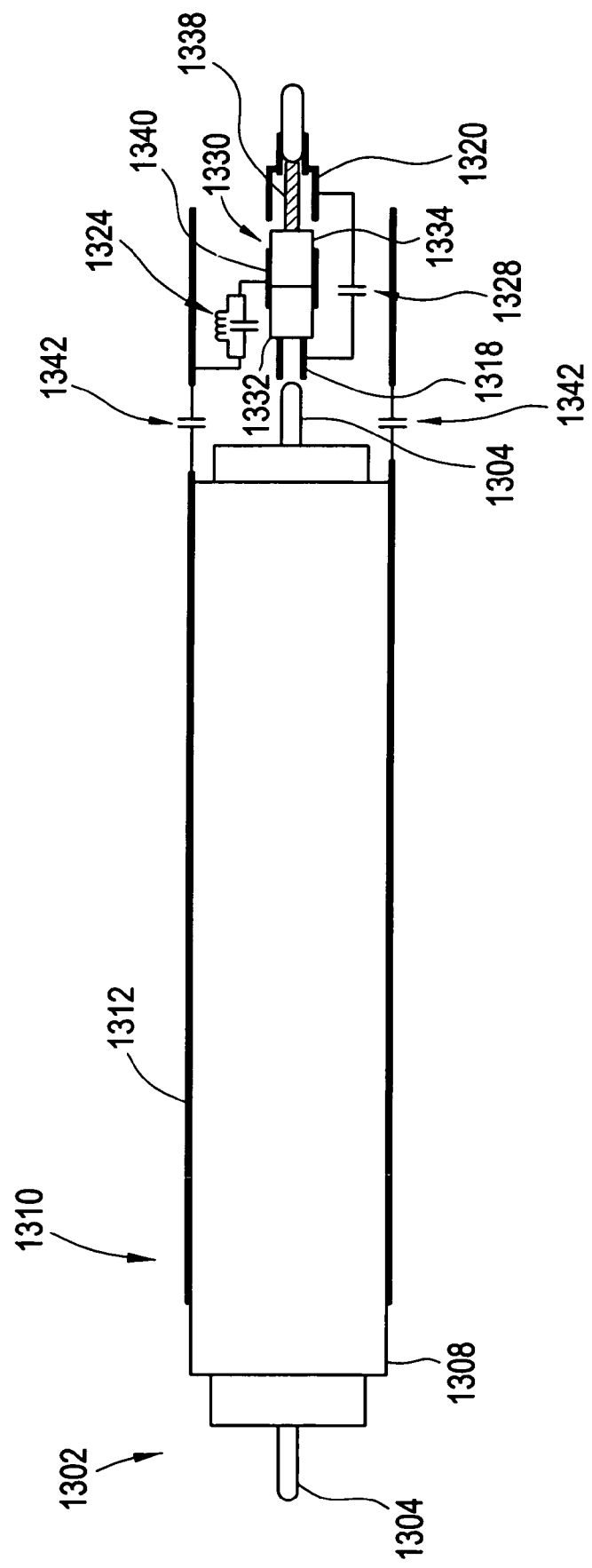
FIG. 13 shows an embodiment of a connector having a connection detector and a DC blocking circuit.

The connector may also include a DC blocking circuit. It may be combined with a connection detector. FIG. 13 depicts another embodiment of a connection detector combined with a DC blocking circuit. The proximal end of the guidewire (1302) having an inner conductor (1304) and outer conductor (1308) may be inserted into the distal end of the connector (1310). As the guidewire (1302) is advanced through the connector, the outer conductor (1308) can contact outer contact (1312). The inner conductor (1304) contacts a distal inner contact (1318) and may be electrically coupled to proximal inner contact (1320) through an RF bypass capacitor (1328). The inner conductor (1304) can make contact with a push button assembly (1330) having a distal insulating block (1332), a conductive midsection block (1334) and, e.g., a proximal element (1338) that may be, e.g., a spring. As the inner conductor (1308) pushes the push button assembly (1330) toward the proximal end of the connector (1310), contact may be made between a detection contact (1340) coupled to detector circuit (1324) and the proximal inner contact (1320). This completes a DC path for the control signals from the MR system through the detector circuit (1324). DC voltage can be blocked from the outer conductor (1308) by the RF bypass capacitors (1342).

The connector may also include an identification system. The identification could help ensure that the proper guidewire and connector combination is being used. In an embodiment, the identification system includes a predefined size and/or shape of the orifice of the connector. This predetermined size and/or shape could be selected to allow insertion and/or secure attachment of only appropriately configured guidewires. In an embodiment, the identification system could include a guidewire sensor that recognizes electrically or electronically encoded parameters in the guidewire, such as resistor values, digital signatures, unique serial numbers, or barcodes printed on the guidewires that may be scanned before use or read during insertion of the guidewire. This could help ensure proper combinations of guidewires and connectors and could also help ensure, if desired, that a particular guidewire, having a unique serial number, is used only one time.

Although certain embodiments of these systems and methods are disclosed herein, it should be understood that other embodiments are envisioned as would be understood by one of ordinary skill in the art. The specific embodiments described herein are provided for illustrative purposes. It is not intended that the invention be limited to those specific embodiments. Rather, it is intended that all variations and modifications as fall within the spirit of the invention be included within the scope.

We claim:

1. A magnetic resonance imaging (MRI) guidewire, comprising:
    a guidewire having a distal end sized and shaped for insertion into a subject and a proximal end sized and shaped for insertion into a connector coupled to an MRI scanner, the guidewire comprising an inner conductor extending at least a major length of the guidewire and an outer conductor coaxially disposed about the inner conductor such that the outer conductor has a larger diameter than a diameter of the inner conductor, the outer conductor extending at least the major length of the guidewire;
    wherein the proximal end of the guidewire comprises:
        an outer conductor contact coupled electrically to the outer conductor, the outer conductor contact having a diameter; and
        an extended section of the inner conductor that extends proximally beyond the outer conductor contact, the extended section of the inner conductor including:
            electrically conductive material disposed at least partially around a portion of the extended section of the inner conductor;
            an inner conductor contact radially disposed over the electrically conductive material such that the inner conductor contact has a diameter equal to the diameter of the outer conductor contact;
            an insulated area interposed axially between the outer conductor contact and the inner conductor contact, the insulated area having an electrically insulating material disposed at least partially around at least a portion of the extended section of the inner conductor;

wherein the distal end of the guidewire defines an antenna configured to detect MRI signals, and wherein the inner and outer conductors are configured to conduct the detected MRI signals to the proximal end of the guidewire.

2. The guidewire of claim 1, wherein the guidewire is sized for insertion into a lumen of an anatomic structure of a subject.

3. The guidewire of claim 2, wherein the guidewire is sized and configured for insertion into a human subject.

4. The guidewire of claim 1, wherein the guidewire is sized and configured for insertion into a blood vessel.

5. The guidewire of claim 1, wherein the major length of the guidewire has a diameter that is less than about 0.04 inches.

6. The guidewire of claim 5, wherein the diameter of the major length of the guidewire is between about 0.012 inches and 0.038 inches.

7. The guidewire of claim 6, wherein the diameter of the major length of the guidewire is about 0.014 inches.

8. The guidewire of claim 1, wherein the diameter of the inner conductor is between about 0.004 inches and about 0.012 inches.

9. The guidewire of claim 1, wherein the guidewire has a stiffness sufficient for insertion into a lumen of an anatomic structure of a subject.

10. The guidewire of claim 1, wherein the guidewire is biocompatible and is sized and shaped for detachable insertion into the connector.

11. The guidewire of claim 1, wherein the guidewire comprises a conductive material.

12. The guidewire of claim 1, wherein the guidewire is composed of nonmagnetic materials.

13. The guidewire of claim 1, wherein the guidewire comprises a superelastic material.

14. The guidewire of claim 13, wherein the superelastic material comprises titanium.

15. The guidewire of claim 13, wherein the superelastic material comprises Nitinol.

16. The guidewire of claim 1, wherein the guidewire comprises a material that is sterilizable.

17. The guidewire of claim 1, wherein the outer conductor contact and the inner conductor contact are each annular in shape.

18. The guidewire of claim 1, wherein the insulated area is annular in shape.

19. The guidewire of claim 1, wherein the diameter of the outer conductor is equal in length to the diameter of each of the inner conductor contact and the outer conductor contact.

20. The guidewire of claim 1, wherein the extended section is configured and arranged to receive an extension attachment for adding length to the proximal end of the guidewire for enabling medical exchanges without removing the guidewire from the subject.

21. An MRI compatible medical coaxial cable, comprising:
opposing proximal and distal ends with the proximal end sized and shaped for insertion into a connector coupled to an MRI scanner, the coaxial cable further comprising an inner conductor extending at least a major length of the coaxial cable and an outer conductor coaxially disposed about the inner conductor such that the outer conductor has a larger diameter than a diameter of the inner conductor, the outer conductor extending at least a major length of the coaxial cable,
wherein the proximal end of the coaxial cable has:
an outer conductor contact coupled electrically to the outer conductor, the outer conductor contact having a diameter; and
an extended section of the inner conductor that extends proximally beyond the outer conductor contact, the extended section of the inner conductor including:
electrically conductive material disposed at least partially around a portion of the extended section of the inner conductor;
an inner conductor contact radially disposed over the electrically conductive material such that the inner conductor contact has a diameter equal to the diameter of the outer conductor contact;
an insulated area positioned to isolate electrically the outer conductive contact from the inner conductive contact, the insulating area comprising an electrically insulating material disposed at least partially around a portion of the extended section of the inner conductor,
wherein the coaxial cable is configured to conduct MRI signals from a distal end portion to the proximal end.

22. The coaxial cable of claim 21, wherein the coaxial cable is a single-use disposable medical device.

23. The coaxial cable claim 21, wherein the diameter of the outer conductor is equal in length to the diameter of each of the inner conductor contact and the outer conductor contact.

24. The coaxial cable of claim 21, wherein the extended section is configured and arranged to receive an extension attachment for adding length to the proximal end of the coaxial cable for enabling medical exchanges without removing the coaxial cable from a subject.

25. A connector assembly comprising:
the MRI guidewire of claim 1; and
a connector comprising a non-magnetic body with a conductive material defining an RF shield and a DC blocking circuit;
wherein the MRI guidewire is configured and arranged to electrically couple to an MRI scanner;
wherein the RF shield and the DC blocking circuit are configured to block DC voltage transmission from the MRI scanner to the MRI guidewire.

26. The connector assembly of claim 25, further comprising an extension attachment coupling the MRI guidewire to the MRI scanner.

27. The connector assembly of claim 25, wherein the MRI guidewire is configured and arranged such that the MRI guidewire is releasably engageable to the connector a plurality of times during an interventional procedure to allow different medical devices to be loaded onto and removed from the MRI guidewire, and wherein the connector includes a wiper in communication with the MRI guidewire to allow the MRI guidewire to slidably advance therethrough to inhibit the introduction of fluids into the connector.

28. The connector assembly of claim 25, wherein the connector is in communication with an MRI interface circuit or includes an MRI interface circuit and is configured to allow transmission of the received MRI signals to the MRI scanner.

29. The connector assembly of claim 25, wherein the connector is releasably attachable to the outer and inner conductors whereby different medical devices can be serially removed from and attached to the MRI guidewire.

30. The connector assembly of claim 25, wherein the connector comprises an MRI scanner interface circuit, and wherein at least one of the MRI guidewire or the connector comprises a connection detector that identifies when the MRI guidewire is disconnected from the MRI scanner interface circuit.

31. The connector assembly of claim 25, wherein the connector includes a guidewire sensor that recognizes an electrically or electronically encoded serial number associated with the MRI guidewire that is unique to a specific MRI guidewire to thereby limit a respective MRI guidewire to a single-use.

32. A connector assembly comprising:
the medical coaxial cable of claim 21; and
a connector comprising a non-magnetic body with a conductive material defining an RF shield and a DC blocking circuit;
wherein the medical coaxial cable is configured and arranged to electrically couple to an MRI scanner;
wherein the RF shield and the DC blocking circuit are configured to block DC voltage transmission from the MRI scanner to the medical coaxial cable.

33. The connector assembly of claim 32, wherein the connector is sized and configured to receive the proximal end of the coaxial cable and is in communication with an MRI interface circuit and is configured to allow transmission of received MRI signals from a distal end portion of the coaxial cable to the MRI scanner.

34. The connector assembly of claim 32, wherein the connector comprises electrical non-magnetic conductive shielding configured to inhibit RF interference when the guidewire is in operative use with the MRI scanner, and wherein the coaxial cable is configured to be inserted into a patient.

35. The connector assembly of claim 32, wherein the connector comprises an MRI scanner interface circuit, and wherein at least one of the coaxial cable or the connector comprises a connection detector that identifies when the coaxial cable is disconnected from the MRI scanner interface circuit.

\* \* \* \* \*